(12) United States Patent
Zülli et al.

(10) Patent No.: US 6,342,486 B1
(45) Date of Patent: *Jan. 29, 2002

(54) POLYMER GLUCAN ETHER DERIVATIVES, THEIR MANUFACTURING AS WELL AS THEIR USE

(75) Inventors: Fred Zülli, Küttigen; Franz Suter, Döttingen, both of (CH)

(73) Assignee: Mibelle AG Cosmetics, Buchs (CH)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/896,926

(22) Filed: Jul. 18, 1997

(30) Foreign Application Priority Data

Jul. 19, 1996 (DE) .......................... 196 29 117

(51) Int. Cl.[7] .......................... A61K 31/715; C07H 1/00
(52) U.S. Cl. .......................... 514/54; 514/844; 514/860; 514/863; 514/864; 536/120; 536/123.12; 536/124
(58) Field of Search .......................... 514/54, 844, 860, 514/863, 864; 536/120, 123.12, 124

(56) References Cited

U.S. PATENT DOCUMENTS

| | | | |
|---|---|---|---|
| 4,454,315 A | * | 6/1984 | Sasaki et al. ............... 536/18.2 |
| 5,653,967 A | * | 8/1997 | Murphy ..................... 424/70.1 |

FOREIGN PATENT DOCUMENTS

| | | | |
|---|---|---|---|
| EP | 819703 | * | 1/1998 |
| JP | 03-204804 | * | 6/1991 |
| JP | 03204804 | * | 9/1991 |
| WO | 98/17246 | * | 4/1998 |
| WO | 98/40082 | * | 9/1998 |

OTHER PUBLICATIONS

Autio, Karin, "Functional Aspects of Cereal Cell Wall Poly–saccharides", from *Carbohydrates in Food* (Ed. by Ann–Charlotte Eliasson), publ. Marcel Dekker, Inc., pp. 243–253.*

Nikitin, N. *The Chemistry of Cellulose and Wood*, (Chapter IV–A General Survey of Physicochemical Properties of Cellulose), publ. Israel Program for Scientific Translations, Ltd., pp. 62–71.*

Zulli et al., "Carboxymethylated beta (1—>3) glucan. A beta glucan from baker's yeast helps protect skin", Cosmetic Toiletries, vol. 111(12): 91–92 and 95–98, 1996.*

Mansell, P.W.A. "Polysaccharides in Skin Care", Cosmetic & Toiletries, vol. 109: 67, 68, 70 and 72, 1994.*

* cited by examiner

*Primary Examiner*—Ralph Gitomer
*Assistant Examiner*—Devesh Khare
(74) *Attorney, Agent, or Firm*—Proskauer Rose LLP

(57) ABSTRACT

A method for treatment of skin includes topical application of a composition containing a therapeutically effective amount of a 1,3-beta-glucan ether derivative. Such application effectively provides treatment and/or prophylaxis of various skin-related problems, such as neurodermatitis and psoriasis, and reduces the evidence of aging by minimizing wrinkles. In an advantageous embodiment, the glucan ether derivative is present in the composition in a range of concentration of about 0.002% to about 8% by weight. In another embodiment the glucan ether derivative is advantageously carboxymethyl glucan sodium salt.

11 Claims, 3 Drawing Sheets

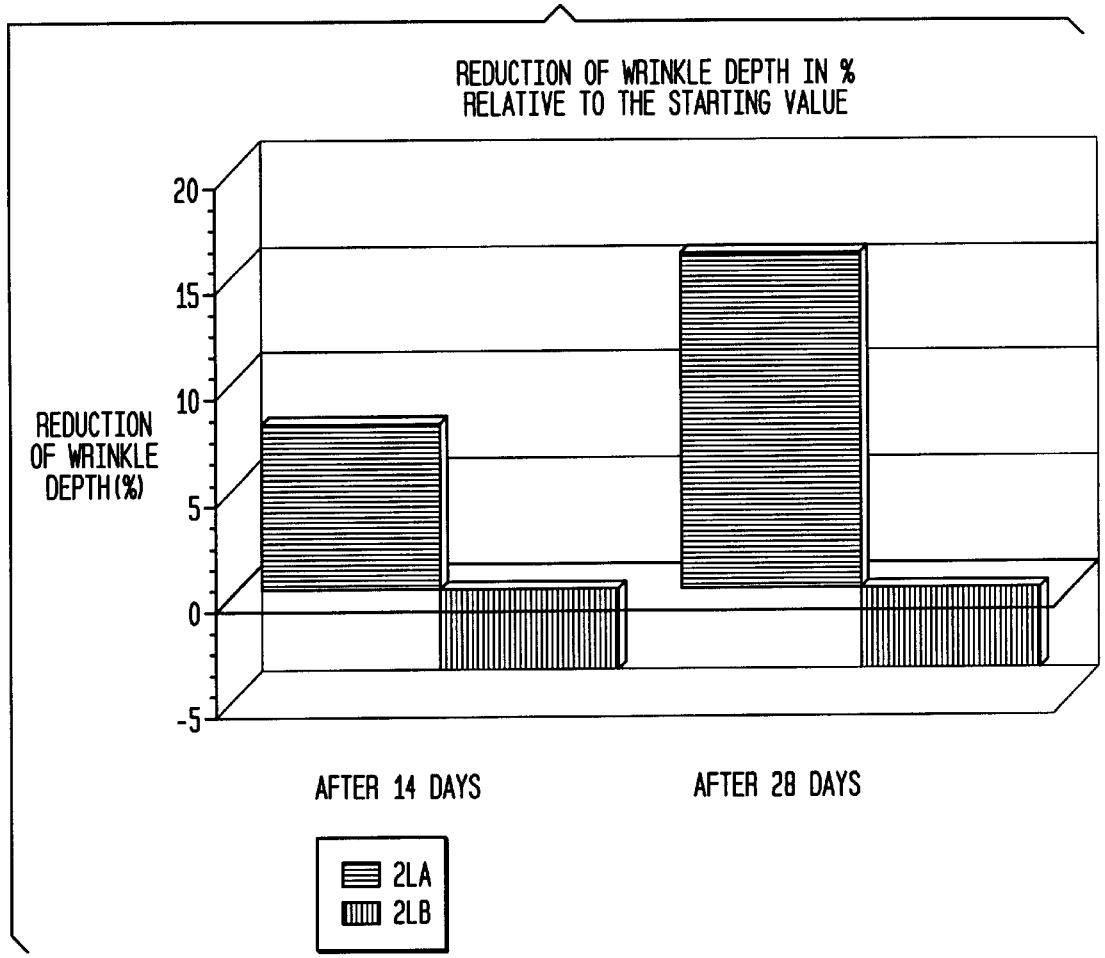

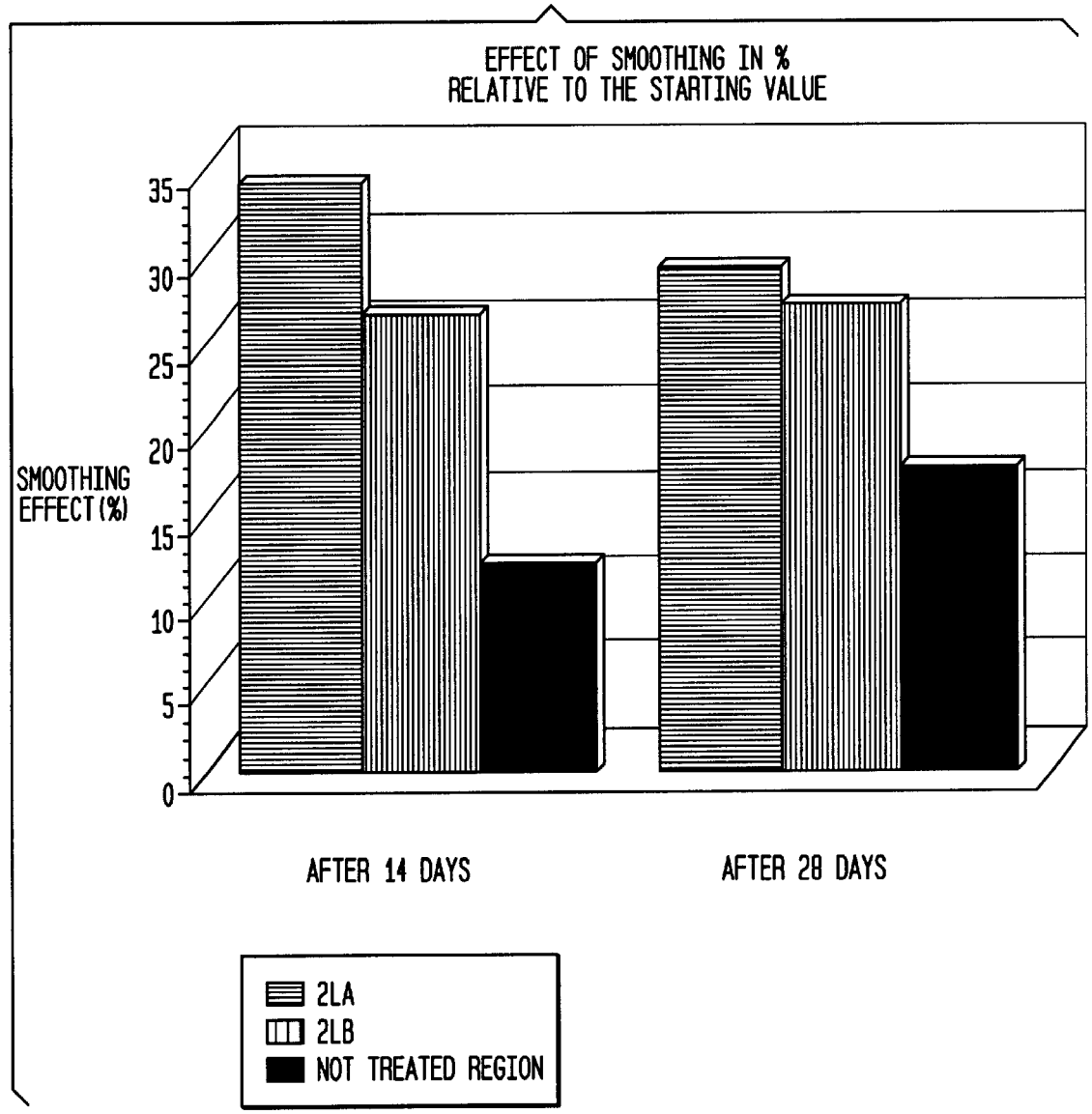

Figure 1:
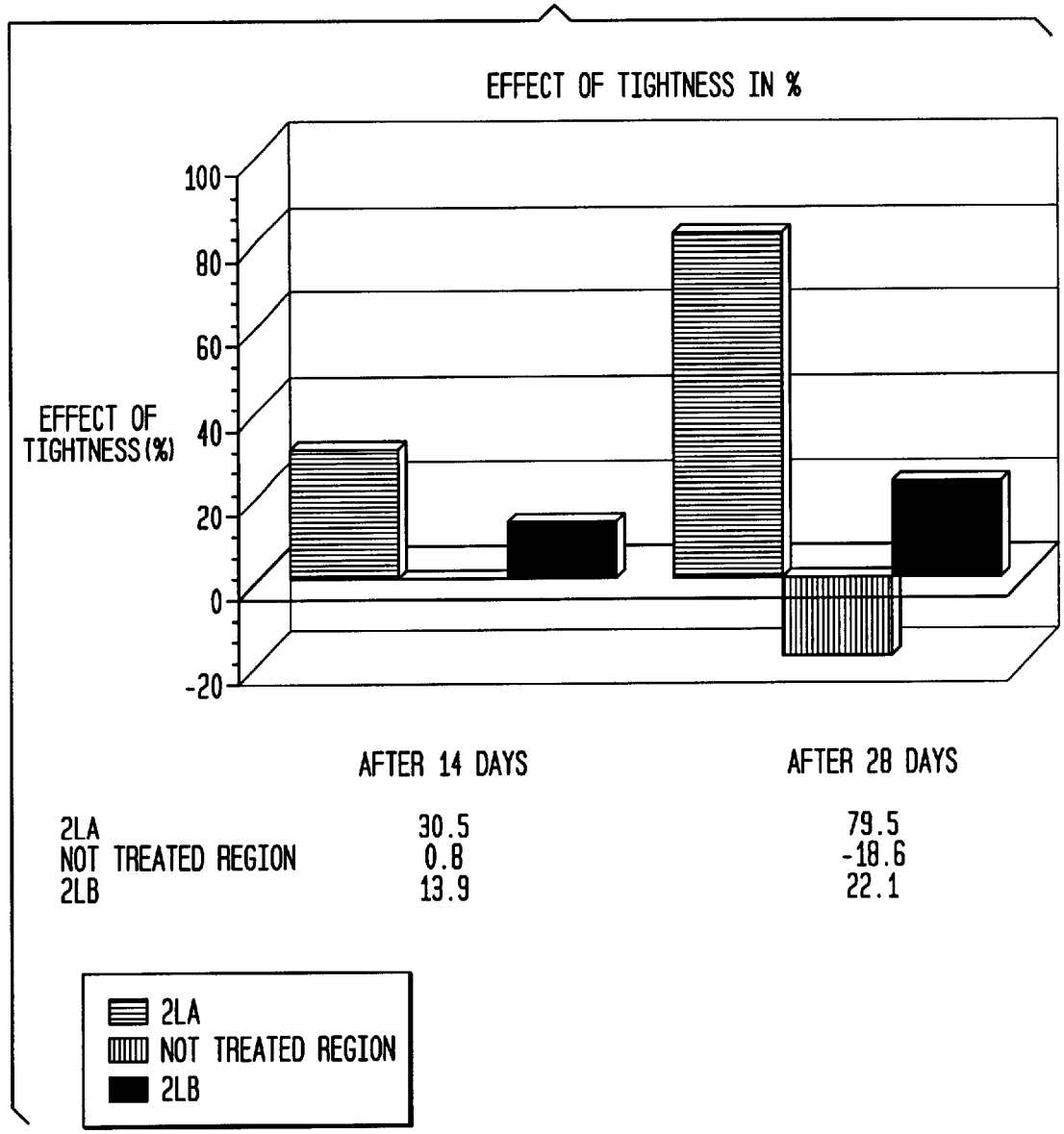

POLYMER GLUCAN ETHER DERIVATIVES, THEIR MANUFACTURING AS WELL AS THEIR USE

The present invention is directed to polymer glucan ether derivatives, to a method for the manufacturing of such glucan ether derivatives as well as to the use of these glucan ether derivatives.

Glucan is a 1,3-beta-polyglucose and is obtained by an alkaline and acid pulping from yeast cells, as this is described, for example, in the U.S. Pat. No. 5,397,773, the U.S. Pat. No. 5,250,436 or the U.S. Pat. No. 5,223,491.

The main disadvantage of the thus isolated glucan is that the glucan has an extremely low solubility in aqueous systems, so that it was only a limited use, for example, in aqueous pharmaceutical and/or cosmetical preparations.

The present invention has the object of providing a polymer compound on the basis of glucan, this polymer compound having an essentially better solubility in aqueous systems than glucan.

This object is realized according to the invention by a polymer glucan ether derivative with the significant characteristics of patent claim 1.

The inventive polymer glucan ether derivatives have, in addition to the monomer units of the formula I, also such monomer units of the general formula II.

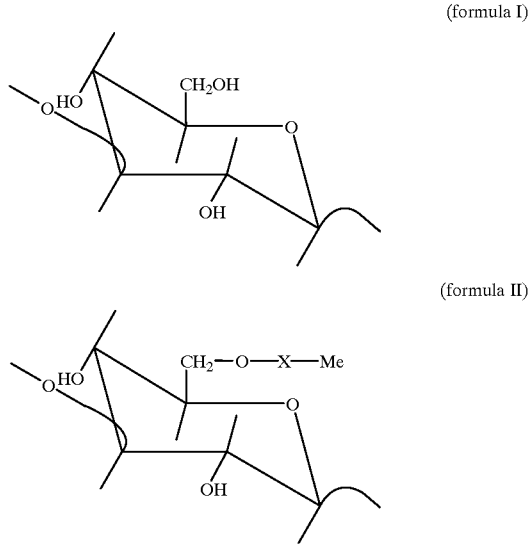

(formula I)

(formula II)

Hereby the monomer units of the formula I are connected with the monomer units of the formula II by a 1,3-beta-glycosidic bond, whereby in formula II X means a —$CH_2$—COO-group, a —$CH_2$—$CH_2$—COO-group, a

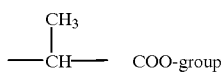  COO-group and/or a —$CH_2$—$CH_2$—$SO_3$-group and Me means hydrogen, an alkali- and/or an alkaline-earth metal.

The inventive polymer glucan ether derivatives have a superior water solubility, whereby, depending on the group X and on the group Me in formula II, this water solubility is higher by the factor 100 to about 500 than the water solubility of the glucan. This extremely high water solubility of the inventive glucan ether derivatives, which absolutely lies at up to 80 g per liter of water, leads to the fact that the inventive glucan ether derivatives can be easily used as active substance in pharmaceutical and/or cosmetical preparations, whereby such pharmaceutical and/or cosmetical preparations are applied preferably in a topical manner and used for the therapy and/or the prophylaxis of skin diseases, skin damages, skin irritations and skin aging, as this is subsequently explained in detail.

The inventive glucan ether derivatives can also be manufactured in a relatively simple and very gentle way, as this is subsequently described in the inventive method.

The inventive glucan ether derivatives preferably have a molecular weight of between 20,000 and 2,000,000, preferably between 50,000 and 500,000.

The good water solubility of the inventive glucan ether derivatives does not only depend on the group designated with X and Me and mentioned above in the formula II, but also on the average degree of substitution, whereby the average degree of substitution for the inventive glucan ether derivatives varies between 0.4 and 0.9, preferably between 0.6 and 0.8. Particularly when the medium average degree of substitution is 0.75 and when in the formula II X means a —$CH_2$—COO-group and Me means sodium, such a carboxymethyl glucan sodium has a perfect water solubility which lies in the range of about 40 g/l of water. For that reason this special glucan ether derivative is preferably used for the manufacturing of topically applicable, pharmaceutical and/or cosmetical composition, as this is subsequently explained in detail.

In respect to the inventive glucan ether derivatives, the residue designated with Me in the formula II can basically mean hydrogen, an alkali metal and/or an alkaline-earth metal. Particularly when in formula II Me means an alkali metal, preferably sodium, such a concrete glucan ether derivative has a high skin tolerance, so that this glucan ether derivative does not cause skin irritations, even not for sensitive users.

This is also the case for such glucan ether derivatives for which in the formula II X means a —$CH_2$—COO-group and/or the —$CH_2$—$C_2$—$SO_3$-group, whereby it could be noted that these specific glucan ether derivatives furthermore have, in addition to the good water solubility and high skin tolerance, ideal characteristics of an active substance, so that such glucan ether derivatives are used preferably in topically applicable, pharmaceutical and/or cosmeticate preparations which are used for the therapy and/or the prophylaxis of skin diseases, akin damages, skin irritations and skin aging.

The present invention is furthermore directed to a method with which the above mentioned glucan ether derivatives can be manufactured in a particularly simple way.

This object is realized according to the invention by a method with the significant characteristics of patent claim 1.

The inventive method for the manufacturing of polymer glucan ether derivatives comprising in addition to the monomer units of the formula I also such monomer units of the general formula II,

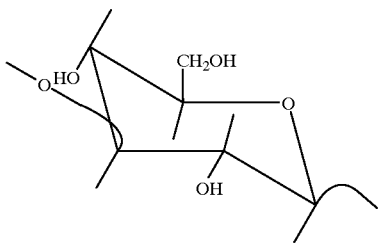

(formula I)

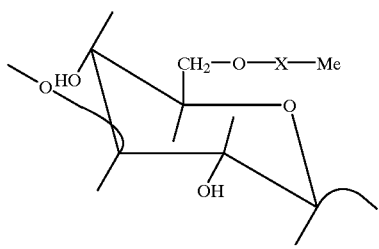

(formula II)

whereby the monomer units of the formula I are connected with the monomer units of the formula II by a 1,3-beta-glycosidic bond and whereby in formula II X means a —$CH_2$—COO-group, a —$CH_2$—$CH_2$—COO-group, a

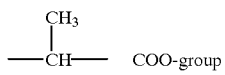 COO-group and/or a —$CH_2$—$CH_2$—$SO_3$-group and Me means hydrogen, an alkali- and/or an alkaline-earth metal, provides that a) a purified and mainly lipid-free glucan is treated in a low alcohol, preferably in isopropanol, by adding an alkaline solution, b) hereafter a part of the alkaline solution is removed, c) the emerging suspension is heated to a temperature of between 40° C. and 60° C. and subsequently converted at this temperature into a glucan ether derivative by adding an aqueous solution of a salt of a haloacid or a halogen sulpho acid of the following formulas III Y—$CH_2$—COO Me, Y—$CH_2$—$CH_2$—COO Me,

 COO Me and/or

Y—$CH_2$—$CH_2$—$SO_3$ Me, whereby in the formulas III Y means a halogen and Me means an alkali- and/or alkaline-earth metal, d) after a reaction time of one hour to four hours the thus formed glucan ether derivative is washed and e) the washed glucan ether derivative is gently dried.

Firstly, the inventive method has the essential advantage that it can be carried out in a relatively simple way and with a low requirement of equipments. Moreover, it was noted that, according to the above described inventive method, the polymer glucan ether derivatives indicated in the formulas I and II can be manufactured in a particular gentle way and with a high purity, so that correspondingly the inventive glucan ether derivatives are rapidly available. In the inventive method undesired side reactions do also not occur, as for example an undesired splitting of the 1,3-beta-glycosidic bond, which leads to the fact that the inventive glucan ether derivatives can be reproducibly manufactured and that they do not comprise undesired side products. The inventive glucan ether derivatives can thus be perfectly used for pharmaceutical and/or cosmetical preparations, as this is subsequently described in detail.

Generally in the inventive method the treatment, which is mentioned in the above indicated step a), of the purified and mainly lipid-free glucan, can be carried out at any temperature, whereby, however, it is particularly advantageous when this treatment of the purified and mainly lipid-free glucan is carried out at room temperature, meaning at a temperature range of between about 16° C. and 22° C. This has the corresponding advantage that undesired side reactions are avoided already in the first reaction step a) of the inventive manufacturing method, so for example an undesired hydrolysis of the 1,3-beta-glycosidic bond, so that correspondingly the reproducibility and the yield of the inventive method is furtherly improved.

If in the inventive method the above mentioned reaction step indicated under point a) is carried out at room temperature, the reaction time is varied, between about 10 hours and 25 hours, preferably between 12 hours and 20 hours, depending on the yield to be obtained of the polymer glucan ether derivative to be synthesized and its purity.

In the inventive method it is described for the above mentioned first reaction step a) that the purified and mainly lipid-free glucan is suspended in a low alcohol. Herefore a $C_1$–$C_4$-alcohol, preferably isopropanol, is used, whereby the mass ratio of glucan to the $C_1$–$C_4$-alcohol, preferably to the isopropanol, varies between 1:10 to 1:30, preferably between 1:15 to 1:25. Such a concrete mass ratio also causes the fact that in this example of the inventive method the glucan suspension is quantitatively converted by the alkaline solution being preferably an aqueous sodium hydroxide solution, which again has an influence on the purity of the thus manufactured inventive glucan ether derivative as well as on the economic efficiency of the inventive method.

In order to suppress in the initially described reaction step a) of the inventive method an undesired side reaction, as for example the splitting of the 1,3-beta-glycosidic bond that the glucan contains, a further development of the inventive method provides that, in exception and/or additionally to the above mentioned temperature range and to the above described reaction times, an aqueous sodium hydroxide solution of 20% by weight to 35% by weight is used as alkaline solution in a mass ratio of glucan to sodium hydroxide solution of between 1:1.5 and 1:3.

In another development of the inventive method a further amount of a low alcohol, preferably a $C_1$–$C_4$-alcohol and particularly isopropanol, is added to the reaction mixture after removing the part of the alkaline solution and before heating the suspension, as this is described above in the reaction step b) of the inventive method, so that subsequently the suspension completed with the corresponding alcohol amount is heated up to a temperature of between 40° C. and 60° C., as this is already described in the reaction step c) of the inventive method. Hereby this measure also serves, on one hand, to suppress the hydrolysis and, on the other hand, to cause an intended reaction in the position 6, so that correspondingly glucan ether derivatives of high purity can be manufactured by applying this variant of the inventive method.

In the above described development of the inventive method it is basically possible that the added amount of the low alcohol does not correspond with the amount of the partially removed alkaline solution, whereby, however, it was noted that particularly high yields can be obtained by the inventive method when the added amount of the low alcohol does correspond with the amount of the partially removed alkaline solution.

Under point d) of the inventive method it is provided that according to the inventive method the manufactured glucan ether derivative is washed after the expiration of the reaction time for between 1 hour and 4 hours. For washing the glucan ether derivative manufactured according to the inventive method basically each suitable organic solvent can be used in which the formed glucan ether derivative is not soluble or soluble only to a certain degree.

A particularly suitable development of the inventive method provides that for washing the glucan ether derivative an alcohol-/water mixture is used, whereby particularly isopropanol-/water mixtures at a volume ratio of isopropanol to water of 1:1 to 1.5:1 are particularly preferred.

In order to safely and reproducibly termination of the reaction time after the expiration of the reaction indicated under point d) of the inventive method, a further development of the inventive method provides that, after the expiration of the reaction time of 1 hour to 4 hours, the reaction mixture is neutralized by adding an acid, preferably by adding a hydrochloric acid, to a pH-value of between 6.8 and 7.5.

In order to isolate in the inventive method the thus manufactured washed and/or neutralized glucan ether derivative from the reaction mixture, the thus manufactured inventive glucan ether derivative being soluble in an aqueous system is precipitated by adding a low alcohol, preferably by adding isopropanol. By this variant of the inventive method the thus manufactured glucan ether derivative can be almost quantitatively removed from the reaction mixture, whereby such an isolated glucan ether derivative then has a high purity.

In respect to the drying that follows the isolation, it is to be noted that this drying of the glucan ether derivative manufactured according to the inventive method has to be carried out preferably in a gentle way. Hereby it was noted that a vacuum drying at temperatures of between 40° C. and 60° C. or a lyophilisation satisfies the requirements, so that such a drying is preferred in the inventive method.

The present invention is directed to the use of the glucan ether derivatives claimed in the patent claims 1 to 5 or of the polymer glucan ether derivatives manufactured according to one of the claims 6 to 16 as active substance in topically applicable, pharmaceutical and/or cosmetical composition.

Moreover, the present invention is directed to topically applicable, pharmaceutical and/or cosmetical compositions, whereby the inventive compositions contain, in addition to the usual ingredients, at least one polymer glucan ether derivative which, in addition to the monomer units of the formula I, comprises also such monomer units of the general formula II,

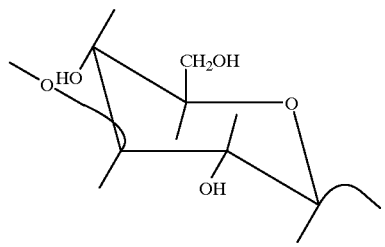
(formula I)

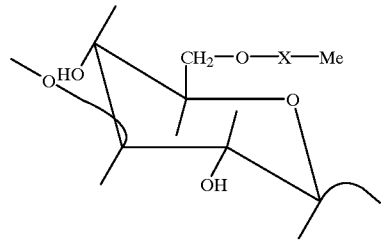
(formula II)

whereby the monomer units of the formula I are connected to the monomer units of the formula II by a 1,3-beta-glycosidic bond and whereby in formula II X means a —CH—COO-group, a —CH$_2$—CH$_2$—COO-group, a

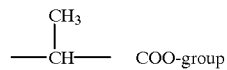
COO-group and/or a —CH$_2$–CH$_2$—SO$_3$-group and Me means hydrogen, an alkali- and/or an alkaline-earth metal.

It was surprisingly noted that the inventive composition, which exists in a form being suitable for the topical application, is perfectly suitable for the therapy and/or the prophylaxis of skin irritations, respectively skin diseases, induced by an oxidative stress in the skin. Such skin irritations, respectively skin diseases, are caused by UVA-radiation, by oxidizing chemicals, by sun radiation or by other environmental impacts. Such skin modifications also occur during the skin aging process, so that the inventive pharmaceutical and/or cosmetical preparations counteracts skin aging.

Furthermore, the present invention is directed to a topically applicable, pharmaceutical and/or cosmetical composition, whereby the composition contains, in addition to the usual ingredients, as active substance at least one glucan ether derivative manufactured according to one of the above described claims 6 to 16. The application fields and advantages are valid which are described above and which are subsequently explained for this inventive composition as well.

The inventive topically applicable, pharmaceutical and/or cosmetical composition comprise the inventive glucan ether derivative, respectively the glucan ether derivative manufactured according to the inventive method, particularly at a concentration of between 0.002% by weight and 8% by weight, preferably at a concentration of between 0.02% by weight and 4% by weight, each relative to the ready-to-apply preparation.

Particularly when the inventive compositions contain the glucan ether derivative or the glucan ether derivative manufactured according to the inventive method being described above in detail and having an average degree of substitution of 0.75, meaning 0.75±0.1, the above described therapeutical and prophylactic characteristics occur in an increased degree. Such an active substance can be described by the general formula V, whereby the molecular weight of this glucan ether derivative varies between 20,000 and 2,000,000, preferably between 50,000 and 500,000. In the formula V X and Me have the same meaning, as indicated above.

Patent Application 196 29 118.6 filed on Jul. 19th, 1996, whereby in the scope of the present disclosure the content of this application is to be considered.

It is described above in connection with the inventive composition that the latter is perfectly suitable for the

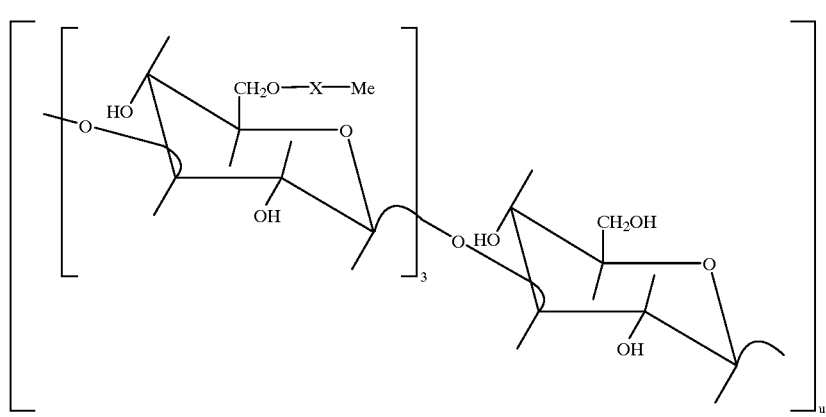

(formula V)

As already explained above, the inventive pharmaceutical and/or cosmetical compositions are particularly applicable for the therapy and/or the prophylaxis of diseases, irritations and/or problems induced by oxidative stress in the skin. Hereby also such diseases, irritations and/or problems are meant which occur during the skin aging process. For example rough skin, missing firmness and elasticity, wrinkles, dry skin and skin scabbing are particularly to be named, whereby subsequently a special use and embodiment of the inventive composition shall be described.

A particularly suitable embodiment of the inventive composition provides that the inventive composition comprises as active substance a carboxymethyl glucan of the following formula VI, therapy and/or the prophylaxis of skin irritations, respectively skin diseases, being induced by an oxidative stress in the skin.

Moreover, it was surprisingly noted that the inventive composition, which contains as active substance the inventive glucan ether derivative or the glucan ether derivative manufactured according to the inventive method, can also be used with a good success as anti-aging agent. It was particularly observed that already after some days of applying the inventive composition a skin tightening, a reduction of the wrinkle depth and a skin smoothening occurred, whereby the users of the inventive composition reported unanimously that the skin treated with the inventive composition feels essentially more elastic and smoother. Con-

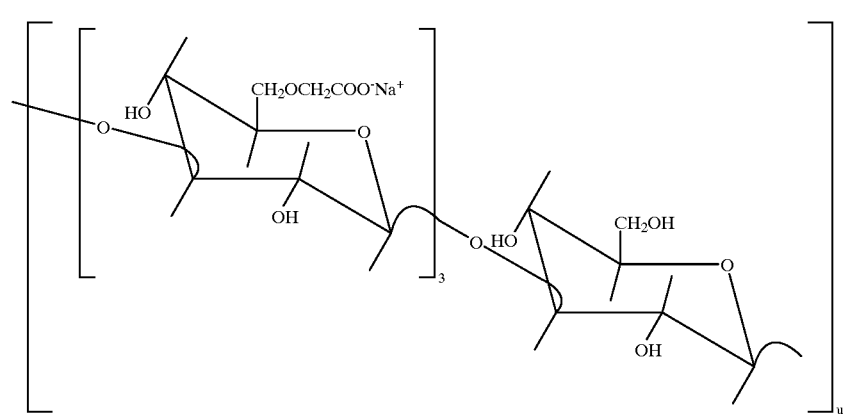

(formula VI)

whereby this carboxymethyl glucan is preferably manufactured in the way as it is claimed above and in the above described patent claims 6 to 16.

The purified and mainly lipid-free glucan used as starting substance in the inventive method can be manufactured according to the known method. It is, however, particularly suitable if the glucan is isolated, as described in the German currently the wrinkle depth and the number of wrinkles were particularly reduced in the areas around the eye, the cheeks and the upper lips. Moreover, it was noted that already after a repeated administrations, as for example after a second till a seventh administration, rough and chapped skin rapidly smoothened, so that correspondingly the inventive composition can also be used for the therapy of rough skin.

Furthermore, the users reported that, in contrary to earlier experiences, rough and chapped skin did not occur even after extremely stressing the skin, so that correspondingly the inventive composition can also be used to avoid the occurrence of rough and/or chapped skin.

Particularly the above mentioned advantages are shown by such an embodiment of the inventive composition that contains between 0.002% by weight and 8% by weight of the inventive glucan ether derivative, between 0% by weight and 3% by weight of an alcohol, particularly an $C_1$–$C_4$-alcohol and preferably ethanol, between 0.5% by weight and 15% by weight of an alkylenglycol, preferably a moderately viscous polyenglycol, between 1% by weight and 3% by weight of a paraffin, preferably of a liquid paraffin, between 5.5% by weight and 9.5% by weight of other additives as well as between 92.988% by weight and 75% by weight of water. Hereby such a composition has a gel-like to cream-like consistency, so that it can be easily topically applied without problems. It was also observed that the above mentioned composition is absorbed by the skin relatively fast after the application, so that an undesired greasy after effect of the composition does not anymore occur already after some seconds up to some minutes after the application of the composition. As further additives the above mentioned composition comprises, for example, stabilizing agents, as particularly hydrated polyisobutene, preservatives, as for example phenoxyethanol and/or imidazolidinyl urea, thickening agents, as for example stearic acid and/or palmitic acid, and perfumes.

The term water used in the above described inventive composition as well as in the subsequent described inventive composition covers all aqueous systems, as particularly deionised water, distilled water, aqueous salt solutions and aqueous buffer systems.

A preferred development of the above described topically applicable, pharmaceutical and/or cosmetical composition comprises as active substance at least one glucan ether derivative, whereby this active substance is chemically composed and manufactured in the way as it is described above for the inventive glucan ether and for the inventive method. Hereby the concentration of the glucan ether derivative preferably lies in the inventive composition at 0.04% by weight, whereby this quantitative indication refers to the weight of the ready-to-apply composition. In the inventive composition particularly the sodium salt of the carboxymethyl glucan is used as glucan ether derivative, whereby this sodium salt of the carboxymethyl glucan is specified in detail and described in the formula VI.

In addition to that it was observed that the inventive topically applicable, pharmaceutical and/or cosmetical composition can be used for healing wounds. After applying the inventive composition once to four times it could be noted that the formation of new tissue occurs more rapidly without causing infections and inflammations. The cicatrisation was also accelerated, whereby the scars treated with the inventive composition were elastic and resistant to tearing. Depending on the cream-like to gel-like consistency of the inventive composition moreover a pleasant cooling of the wound occurred, which was felt to be very pleasant particularly in the case of burns (burn wounds).

A topically applicable, pharmaceutical and/or cosmetical composition for healing wounds particularly comprises a cream-like to gel-like consistency and contains between 0.002% by weight and 1% by weight of the above described glucan ether derivative, between 1% by weight and 3% by weight of panthenol, between 15% by weight and 28% by weight of a fatty, respectively oily additive, as preferably lecithin, propylenglycol, polyethylenglycol ether of higher fat alcohols and triglycerides of higher fatty acids, between 0.05% by weight and 7% by weight of other additives, as preferably alcohols, particularly $C_1$–$C_4$-alcohols, vitamins, particularly vitamin A and/or vitamin E and perfume, as well as between 83.948% by weight and 61% by weight of water.

Particularly good result can be obtained with an embodiment of the inventive composition in the field of wound healing, when this embodiment of the inventive composition comprises between 0.1% by weight and 0.2% by weight of the sodium salt of the carboxymethyl glucan shown and described above in the formula VI. Hereby it was noted that such an embodiment of the inventive composition causes a particularly rapid wound healing, whereby the term wound means all known small wounds with and without the risk of infection, as for example abrasions, small cuts and scratch wounds, chaps, slight burns, sun burn, soreness as well as inflammations of any kind.

In addition to the afore described applications of the inventive composition, it was surprisingly and further observed that the inventive composition is particularly suitable for the therapy and/or the prophylaxis of skin irritations, respectively skin diseases, particularly for the therapy and/or the prophylaxis of neurodermatitis and/or psoriasie.

It is particularly advantageous for such an application of the inventive composition in the field of the afore mentioned skin irritations and/or skin diseases, when the inventive composition comprises, in addition to the active substance on the basis of the above described glucan ether derivative and water, at least one phospholipid as well as at least one oil.

The above described embodiment of the inventive composition, which contains as minimum components water, one phospholipid, one oil and one glucan ether derivative, can exist in any application form being suitable for the topical application, whereby a liquid formulation as emulsion, respectively suspension, and particularly a formulation as nanoemulsion is preferred. In the latter case the inventive composition is thus a nanoemulsion of the at least one glucan ether derivative, of the at least one phospholipid and of the at least one oil in water or in a mixture of water and alcohol, whereby the particle size of the emulsified particles varies between 30 nm and 5.000 nm, preferably between 50 nm and 200 nm.

In respect to this embodiment of the oil containing in the inventive composition, it is to be noted that this is either a single oil or a mixture of oils, particularly a mixture of vegetable liquid oils.

The above described embodiment of the inventive composition preferably contains as oil a mixture of vegetable oils, whereby this mixture of vegetable liquid oils comprises particularly almond oil, avocado oil, calendula oil and/or jojoba oil.

Particularly when the above described, topically applicable, pharmaceutical and/or cosmetical composition being preferably a nanoemulsion, contains between 0.005% by weight and 1% by weight of the glucan ether derivative, as this is described above and/or as this is manufactured according to the inventive method, between 15% by weight and 25% by weight of the oil, particularly a vegetable oil and preferably a mixture of almond oil, avocado oil, calendula oil and/or jojoba oil, between 1% by weight and 5% by weight of a phospholipid, particularly a phospholipid containing between 50% by weight and 90% by weight of phosphatidylcholine, between 0% by weight and 8% by weight of an alcohol, preferably a $C_1$–$C_4$-alcohol, between 8% by weight and 15% by weight of other additives as well as between 75.6% by weight and 46% by weight of water, such a special composition has perfect therapeutical and/or prophylactic characteristics. The above used term "other additives" means particularly preservatives, as preferably phenoxyethanol, vitamins, as preferably vitamin E-acetate, glycerin and perfume.

When the above described, topically applicable, pharmaceutical and/or cosmetical composition is used for the therapy and/or the prophylaxis of skin irritations and/or skin diseases and when this composition is then a nanoemulsion and when it contains particularly the 0.2% by weight of the glucan ether derivative, preferably the sodium salt of the carboxymethyl glucan indicated in the formula VI, such a special composition can be ideally used for the treatment of neurodermatitis and psoriasis, as this was observed in a first study which will be described subsequently.

Altogether it is to be noted that the afore described inventive compositions can perfectly be used with an great success as topically applicable, pharmaceutical and/or cosmetical compositions for the treatment of skin irritations and/or skin diseases being induced by oxidative stress in the skin, as sun protection before or after solar exposure, as daily cream, as body lotion and/or as cleansing composition. Furthermore, it was observed that the inventive composition can also be used as anti-aging agent particularly for the tightening of the skin, the reduction of the wrinkle depth and/or for the therapy and/or the prophylaxis of rough and/or chapped skin. Moreover, it was noted that the inventive composition can be used with great success for the healing of wounds and/or for the therapy and/or the prophylaxis of skin irritations and/or skin diseases, particularly for the therapy and/or the prophylaxis of neurodermatitis and/or psoriasis.

It was described above that the inventive composition comprises as active substance glucan ether derivatives, particularly carboxymethyl glucan, whereby the corresponding monomer units of this glucan ether derivatives are connected with each other by a 1,3-beta-glycosidic bond. This formulation is to comprise also such derivatives the monomer units of which are connected by a 1,3-beta-glycosidic bond in linear way and additionally by a 1,6-beta-glycosidic bond in a branched way, whereby, however, the portion of the branched 1,6-beta-glycosidic bonds is essentially smaller than the portion of the linear 1,3-beta-glycosidic bonds and whereby the portion of the 1,6-beta-glycosidic bonds lays particularly between 0% to 20%, preferably between 4% and 10%, relative to the portion of the 1,3-beta-glycosidic bonds.

The invention is subsequently explained in connection with examples.

Manufacturing of Carboxymethyl Glucan 1 kg glucan was suspended in 20 l isopropanol by stirring in the cold and treated with 2 kg of aqueous sodium hydroxide solution of 30% by weight for 16 hours at room temperature (16° C.–22° C.).

After this alkaline treatment and after a short sedimentation time of 20 minutes 8 l of alkaline aqueous isopropanol supernatant was decanted. Hereafter 8 l of isopropanol were added.

The suspension was then heated up to 60° C. under continues stirring.

After achieving the final temperature 1.5 kg of the sodium salt of the chloroacetic acid being dissolved in 1.5 kg water were added.

After a total reaction time of 2.5 hours at 60° C., the reaction product was sedimented and the supernatant was decanted. Subsequently 4 l of the aqueous isopropanol solution (V:V, 50%:50%) were added.

After having washed the reaction product, the sodium salt of the carboxymethyl glucan was dissolved in 20 l of water. Hereafter a 10 N hydrochloric acid solution was added so that the pH-value of the solution was set to a value of 7.

The sodium salt of the carboxymethyl glucan was precipitated from the neutralized, aqueous solution by adding 40 l of isopropanol.

After separating the precipitated sodium salt of the carboxymethyl glucan it was dried in a vacuum-drying chamber at 60° C.

The yield of sodium salt of the carboxymethyl glucan was 1.3 kg.

The sodium salt of the carboxymethyl glucan was analyzed. Hereby it was observed that the product had a average degree of substitution of 0.75±0.1.

In-Vivo-test of 3 Formulations in Respect to their Effectiveness Against the UVA-induced Oxidative Stress Three different creams were formulated, whereby the creams had the following compositions:

Cream A 1. component: 0.5% phenoxyethanol 0.3% imidazolidinyl urea 0.02% triethanolamine 2% alcohol 1% propylene glycol 87.66% aqua 2. component: 4% PEG-5 glyceryl stearate 1% cetyl alcohol 1% stearic acid 2% paraffinum liquidum 0.5% hydrogenated polyisobutene 3. component: 0.02% perfume Cream B 1. component: 0.5% phenoxyethanol 0.3% imidazolidinyl urea 0.02% triethanolamine 2% alcohol 1% propylene glycol 0.2% sodium carboxymethyl betaglucan 87.46% aqua 2. component: 4% PEG-5 glyceryl stearate 1% cetyl alcohol 1% stearic acid 2% paraffinum liquidum 0.5% hydrogenated polyisobutene 3. component: 0.02% perfume Cream C 1. component: 0.5% phenoxyethanol 0.3% imidazolidinyl urea 0.02% triethanolamine 2% alcohol 1% propylene glycol 0.04% sodium carboxymethyl betaglucan 87.62% aqua 2. component: 4% PSG-5 glyceryl stearate 1% cetyl alcohol 1% stearic acid 2% paraffinum liquidum 0.5% hydrogenated polyisobutene 3. component: 0.02% perfume The above mentioned %-indications all refer to % by weight and the used product designations correspond to the INCI-declaration, as they are mentioned in the "International Cosmetic Ingredient Dictionary", 1995, published by "The Cosmetic, Toiletry, and Fragrance Association", Washington.

For the manufacturing of the creams A to C it was uniformly proceeded as follows:

Each first component was filled into a reactor and heated up to about 60° C. The second component heated up to about 70° C. was added under continuos stirring. The combined components were then homogenized in the reactor. Subsequently to that the mixture was cooled down to about 35° C. under stirring. Having reached this temperature the third component was added and the mixture cooled down to 25° C. under stirring.

About 2 mg/cm$^2$ of each cream A to C were administered on defined skin areas (diameter of about 2,5 cm) on the inner side of the lower arm of 10 volunteers twice a day for 5 days. Two fields remained untreated and served as control.

A radiation with UVA-light (10 J/cm$^2$; radiation source: Multiport, Model 601, Solar Light, USA) was carried out on the fifth day 30 minutes after the last application of the cream A to C. One test field each was not radiated.

After extracting the squalene and the squalene hydroperoxide with 1 ml of ethanol, the concentrations of the squalene and the squalene hydroperoxide were determined by high-pressure liquid chromatography in the extracts of the differently treated defined skin areas.

The squalene determination was carried out according to H. P. Nissen et al, Chromatographia 11/12; 686–690, 1990, whereby for the determination the following HPLC-conditions were maintained:

flow rate: 1 ml/min column: LiChrospher RP 18 (5 μm); 4.6×125 mm eluent; Acetonitril/i-propanol (50/50)

detection: 210 nm

The determination of the squalene hydroperoxide was carried out according to J. R. Zhang et al, Free Radic. Biol. Med. 1:1–10; 1995, A. E. Holley et al, Free Rad. Res. Comms. Vol. 15., No. 1., 51–63,; 1991 and C. Colin et al, IFSCC-conference 1994, Venice, A 105, whereby a postcolumn derivatisation was carried out with isoluminol/microperoxidase, whereby the detection was carried out with chemiluminescence. Herefore the following conditions were valid:

flow rate: 1 ml/min column: LiChrospher RP-Select B (5 μm); 4.6×125 mm eluent: methanol derivati-isoluminol (1 mM) and sation-microperoxidase (10 μg/ml) dissolved in reagent: 100 mM Borate-buffer (pH 10)/methanol (70/30)

flow rate/ derivatisationreagent: 0.8 ml detection: chemiluminescence

As a result of the examination it is to be noted that in the extracts obtained from the skin areas treated with the creams B and C only small amounts of squalene hydroperoxide could be found. Contrarily to that, larger amounts of squalene hydroperoxide could be analyzed in such extracts obtained from the skin areas treated with the cream A and from the untreated skin areas after the radiation.

Since squalene hydroperoxide is formed by reactive oxygen species, it can be concluded from these result that the cream B and C which comprise the active substance sodium salt of the carboxymethyl glucan are able to clearly reduce the formation of squalene hydroperoxide by free radicals.

In the following table 1 the results of the examination are expressed as percentage inhibition of the peroxidation of the areas treated with the creams B and C relative to the area treated with cream A.

TABLE 1

| product | inhibition of the peroxidation (in %) relative to the skin areas treated with cream A |
|---|---|
| cream B | 94.9 |
| cream C | 58.9 |

The inhibition of the peroxidation indicated above in table 1 is calculated as follows:

100×(SQOOH (cream A)–SQOOH (cream B or cream C))/SQOQH (cream A)

SQOOH=squalene hydroperoxide concentration/squalene concentration

No skin intolerance or skin irritation was observed during, neither in the case cream B nor in the case of cream C, during the application on 10 test persons being between 18 and 40 years old.

In-Vivo-test of Two Formulations in Respect to their Effectiveness as Anti-aging Preparation For the detection of the effectiveness of composition containing glucan ether derivatives two cream-like formulations were examined, whereby the subsequently indicated cream-like composition being designated with 2LA contains as active substance the sodium salt of the carboxymethyl betaglucan, as this characterized above by the formula VI, whereas the normally identically constructed, cream-like composition designated with 2LB did not contain the afore mentioned active substance.

The two examined composition 2LA and 2LB, which were manufactured analogously to the above described example, comprised the subsequently listed ingredients, whereby the product designations correspond to the INCI-declaration, as it can be read in the afore mentioned dictionary.

| INCI-name | 2LB % by weight | 2LA % by weight |
|---|---|---|
| aqua | 87.5 | 87.46 |
| alcohol | 2 | 2 |
| polypropylene glycol | 1 | 1 |
| sodium carboxymethyl betaglucan | 0 | 0.04 |
| phenoxyethanol | 0.5 | 0.5 |

-continued

| INCI-name | 2LB % by weight | 2LA % by weight |
|---|---|---|
| imidazolenidinyl urea | 0.3 | 0.3 |
| PEG-5 glyceryl stearate | 4 | 4 |
| cetylalcohol | 1 | 1 |
| stearic acid/palmitic acid | 1 | 1 |
| paraffin | 2 | 2 |
| hydrogenated polyisobutene | 0.5 | 0.5 |
| perfume | 0.2 | 0.2 |

Ten healthy female test persons of between 61 and 75 years applied twice a day over a time period of 28 days the above described composition 2LA and 2LB on selected test areas on the inner side of the lower arm and in the face in the regions of the eyes.

In the beginning of the examination the skin elasticity, the fold depth and the skin roughness were measured before the first application of the composition, whereby these afore mentioned three parameters were repeated on day 14 and on day 28 after the administration.

The test persons were obliged not to apply any other external agents on the test areas three days before the beginning of the examination and during the whole examination time (28 days). Only water was admitted to be used for the cleansing.

The last measuring after day 26 was carried out 8 hours after the last administration of the corresponding product.

The test areas of the inner aides of the lower arm were radiated twice a week with a sun simulator with 0.75 MED (minimum erythemdose). The afore mentioned parameters were measured as follows:

a) Measuring of the Skin Elasticity (Skin Tightening)

The skin elasticity was measured with a Cutometer SEM 474 (Manufacturer: Courage & Khazaka Electronic GmbH, Cologne). Hereby the skin surface was sucked into the opening (2 mm, inner diameter) of a special probe by vacuum. The entering depth of the skin into the probe was optically measured without mechanical influence. The measurings were carried out with a constant vacuum (500 mbar) at a measuring time of 1 second. Subsequently to that the vacuum was turned off for 1 second and the measuring cycle was repeated fifty times.

For the analysis the 50 minimum and the 50 maximum amplitudes were used. The data record (for each test person and each measuring day) a logarithmic function of the type $y=1/a (\ln x+b)$ was adapted, whereby $x$=maximum amplitude, respectively minimum amplitude and $y$=Amount of measuring cycles. This adaptation was realized by minimizing the sum of the remaining values for the adapted curve (program: Statgraphics Plus for Windows-Version 3.0—Manugistics, USA).

For all adaptations the value of the coefficient of correlation was larger than 0.9. The values of a and b of the individual, logarithmic function were then measured for each test area and each measuring moment. The logarithmic functions were drawn from the average values and compared to each other. The surfaces under the functions were calculated (Program: Mathcad 6.0 Mathsoft, USA) for the maximum values as well as for the minimum values by forming the integral between 0 and 100 to $$y=\int (\ln x+b)/a \, dx = (bx+x\ln x)/a$$

b) Measuring of the Fold Depth

The determination of the fold depth was carried out with the skin surface measuring device OFR 01 (Romano GmbH, Cologne). The determination of the fold depth was carried out with the help of the profile method of measuring. For the description of the fold depth the parameter Rt (DIN 4768/1) was selected. Rt is the maximum roughness depth, meaning the distance between the line of the elevation and the line of the indentation within the measuring path. Since it is not possible to measure directly on the surface of the skin, corresponding skin impressions were generated with Silasoft N (Manufacturer: Detax-Dentol, Karlsruhe) and measured in the following conditions:

| Measuring path: | 15,000 μm |
|---|---|
| analyzable path: | 12,500 μm |
| step size: | 2.5 μm |
| total steps: | 5,000 |
| number of measuring per impression: | 11 | c) Measuring of the Skin Roughness

The determination of the skin roughness was carried out with the Skin Visiometer VS 400 (Courage & Khazaka Electronic GmbH, Cologne).

The measuring principle is based on the transillumination of a very thin, specifically colored silicon skin impression. Hereby the light is correspondingly absorbed by the silicon material relative to its strength. The silicon skin impression pictures the heights and the depths as negatives, which means that the skin folds are higher in their impression and the silicon material is correspondingly thicker at this area. This method is based on the absorption law of Bouguer-Lambert.

By making the light absorptions visible, as for example by a black/white CCD-camera on a PC-monitor, it is possible to describe the height and the depth of each point of the impression by a corresponding classification in a gray scale value. The distance of each point to the base line of the skin impression can be calculated in mm by the specially developed technique of picture digitizing and by the software of the Skin visiometers vs 400.

The thus obtained measuring values were transmitted into a calculator after carefully verifying the plausibility and securing the quality. The analysis was realized by aid of the software "Statgraphics" for Windows, Version 3.0—Manugistics, USA. In addition to the descriptive statistics, the "Wilcoxon matched pairs signed rank test" was carried out, whereby $p \leq 0.05$ functions as indication for a statistic difference.

As the result of the afore mentioned examination it is to be noted that the application of the product 2LA leads after 25 days to a statistically significant skin roughening compared to the starting situation and compared to the untreated situation. Moreover, the application of the composition 2LA causes a statistically significant reduction of the fold depth in comparison with the starting situation, whereas the skin roughness also decreases in a statistically guaranteed manner.

Furthermore, the test results clearly show that the composition 2LA is essentially superior to the composition 2LB.

These afore mentioned statements are quantified by the following FIGS. 1 to 3.

In-Vivo-test of Two Formulations in Respect to their Effectiveness for the Treatment of Psoriasis and Neurodermatitis A microemulsion was manufactured which contained the following ingredients:

| INCI-name | % by weight |
| --- | --- |
| lecithin | 2.5 |
| alcohol | 6 |
| sweet almond oil | 10 |
| avocado oil | 5 |
| calendula oil | 5 |
| tocopheryl acetate | 0.1 |
| glycerin | 10 |
| aqua | 60.6 |
| polypropylene glycol | 0.5 |
| phenoxyethanol | 0.1 |
| sodium carboxymethyl betaglucan | 0.2 |
| perfume | 0.01 |

The afore indicated designations of the ingredients was realized according to the INCI-declaration, as this is mentioned in the above cited dictionary.

With this formulation being subsequently designated with composition D firstly a 31 year old woman, whereby this patient suffered from *Psoriasis guttata*. Hereby the back of the right hand, the left small finger, both legs (inner side and outer side several 1 cm large areas), the left leg (5 cm large area above the inner foot ankle caused by strong burns of second degree) as well as the whole upper part of the body were infected with smaller sources of contagion, whereby in addition to that both elbows were strongly encrusted.

For the treatment cream was applied on the infected areas until a saturation point of the skin was obtained.

Already after a treatment of four days the infected areas on the back of the right hand except a very small spot were healed. On both legs a clear reduction of the skin redness and the infection was observed. The source of contagion of 5 cm also showed an obvious healing and a clear reduction of the skin redness.

The patient reported a subjectively felt, good skin feeling and her smooth skin after having applied the composition D.

A 43 year old woman suffering from psoriasis since 30 years and who had within the last 10 years only single, sporadically occurring sources of contagion on the elbows and the scalp, reported that she obtained an immediate healing of the sporadically occurring sources of contagion within some days by applying the composition D. By reasons of this positive result the patient decided not to apply anymore the cortisone cream that she used before, since the composition D showed better results for the healing of immediately occurring psoriasis infections than the originally applied cortisone cream.

A 33 year old man suffering from 1 cm large, inflammable and squamous spots being spread over the front head and extending into the hair line and behind the ears, applied the composition for about 2 months. Hereby the application of the composition D was realized daily after taking a shower. Already after applying the composition D for one week, it was observed that the inflammable, squamous spot had almost disappeared, whereby after finishing the treatment with the composition D the sources of contagion reappeared almost immediately. The patient moreover reported that after having applied the composition D he felt a clear relief of the itching, whereby furthermore by means of the application of the composition D the patient had a very positive skin feeling.

A 17 year old man suffering from neurodermatitis which could clearly be noted on the body was treated twice a day with the composition D for 2.5 weeks. After the treatment time the neurodermatitis had completely disappeared. As soon as the treatment with the composition D, however, was finished, the neurodermatitis reappeared immediately. This caused the patient to continue the corresponding treatment, which again caused a healing within a very short time.

A cream-like composition which can be used for the wound healing comprises particularly the following ingredients:

| INCI-name | % by weight |
| --- | --- |
| aqua | 70 |
| sodium carboxymethyl betaglucan | 0.1 |
| panthenol | 2 |
| polypropylene glycol | 0.25 |
| alcohol | 0.5 |
| glycerin | 1 |
| pentylenglycol | 1 |
| methylchloroisothiazolinone | 0.1 |
| allantoin | 0.1 |
| disodium EDTA | 0.1 |
| diisopropyl adipate | 3 |
| rentinyl acetate | 0.5 |
| lecithin | 0.2 |
| caprylic/capric triglyceride | 9 |
| steareth-2 | 3 |
| steareth-21 | 2 |
| tocopheryl acetate | 2 |
| farnesol | 1 |
| stearic acid | 1.5 |
| polyacrylamide | 2.5 |
| perfume | 0.15 |

The designations used above correspond with the declaration, as they are mentioned in the "International Cosmetic Ingredient Dictionary", 1995, published of "The Cosmetic, Toiletry, and Fragrance Association", Washington.

What is claimed is:

1. A method of treating skin for prophylaxis and/or therapy of diseases and/or irritations induced by oxidative stress in the skin, comprising topically applying a composition to the skin, said composition containing as an active ingredient a therapeutically effective amount of at least one glucan ether derivative, said at least one glucan ether derivative comprising respective monomer units of a formula I and a formula II:

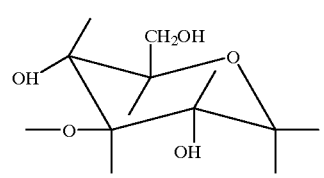

(Formula I)

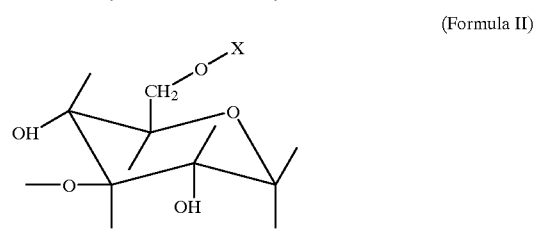

(Formula II)

wherein the monomer units of the formula I are connected with the monomer units of the formula II by a 1,3-beta-glycosidic bond; and in the monomer units of formula II, X is selected from the group consisting of —CH$_2$—COO—Y, —CH$_2$—

$CH_2$—COO—Y, $CH(CH_3)$—COO—Y, —$CH_2$—$CH_2$—$SO_3$—Y, and mixtures thereof, and Y is selected from the group consisting of hydrogen, an alkali-metal, an alkaline-earth metal and mixtures thereof; and wherein said at least one glucan ether derivative comprises a combination of monomer units of formula I and formula II so that there is an average degree of substitution of 0.75±0.1.

2. A method according to claim 1, wherein said therapeutically effective amount is a concentration in a range of about 0.002% to about 8% by weight.

3. A method according to claim 1, wherein said therapeutically effective amount is a concentration in a range of about 0.02% to about 4% by weight.

4. A method according to claim 1, wherein said at least one glucan ether derivative includes at least one monomer of the formula II in which X is —$CH_2$—COO—Y and Y is Na.

5. A method according to claim 1, wherein said therapeutically effective amount is a concentration in a range of about 0.002% to about 8% by weight, said composition further including:

an alcohol in a range of about 0% to about 3% by weight;

an alkylenglycol in a range of about 0.5% to about 15% by weight;

a paraffin in a range of about 1% to about 3% by weight;

other additives in a range of about 5.5% to about 9.5% by weight; and water in a range of about 75% to about 92.988% by weight.

6. A method according to claim 5, wherein said concentration is about 0.04% by weight.

7. A method according to claim 5, wherein said at least one glucan ether derivative is carboxymethyl glucan sodium salt, and said concentration is about 0.04% by weight.

8. A method according to claim 1, wherein said therapeutically effective amount is a concentration in a range of about 0.002% to about 1% by weight, said composition having a cream-like consistency and further comprising:

panthenol in a range of about 1% to about 3% by weight;

a fatty additive in a range of about 15% to about 28% by weight;

other additives in a range of about 0.05% to about 7% by weight; and water in a range of about 61% to about 83.948% by weight.

9. A method according to claim 1, wherein said composition further comprises at least one phospholipid, at least one oil and water.

10. A method according to claim 1, wherein said composition is a nanoemulsion of at least one phospholipid and at least one oil, and of said at least one glucan ether derivative.

11. A method according to claim 1, wherein said therapeutically effective amount is a concentration in a range of about 0.05% to about 1% by weight, said composition further comprising:

an oil in a range of about 15% to about 25% by weight;

a phospholipid in a range of about 1% to about 5% by weight;

an alcohol in a range of about 0% to about 8% by weight other additives in a range of about 8% to about 15% by weight; and water in a range of about 46% to about 75.9% by weight.

* * * * *